United States Patent
Leussler

(10) Patent No.: US 11,946,990 B2
(45) Date of Patent: Apr. 2, 2024

(54) MAGNETIC RESONANCE IMAGING SYSTEM WITH PROTECTION FROM OVERHEATING

(71) Applicant: KONINKLIJKE PHILIPS N.V., Eindhoven (NL)

(72) Inventor: Christoph Günther Leussler, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/790,771

(22) PCT Filed: Nov. 8, 2021

(86) PCT No.: PCT/EP2021/080860
§ 371 (c)(1),
(2) Date: Jul. 5, 2022

(87) PCT Pub. No.: WO2022/101110
PCT Pub. Date: May 19, 2022

(65) Prior Publication Data
US 2023/0333179 A1    Oct. 19, 2023

(30) Foreign Application Priority Data

Nov. 13, 2020  (EP) .................................... 20207417

(51) Int. Cl.
*G01R 33/28* (2006.01)
*A61B 5/055* (2006.01)
(Continued)

(52) U.S. Cl.
CPC ............ *G01R 33/288* (2013.01); *A61B 5/055* (2013.01); *G01R 33/34015* (2013.01); *G01R 33/3692* (2013.01)

(58) Field of Classification Search
CPC ............ G01R 33/288; G01R 33/34015; G01R 33/3692; A61B 5/055
See application file for complete search history.

(56) References Cited

U.S. PATENT DOCUMENTS 9,945,916 B2 *  4/2018  Matschl ............ G01R 33/34015
11,193,991 B2 * 12/2021  O'Neill .............. G01R 33/3692
(Continued)

FOREIGN PATENT DOCUMENTS

EP    2757385 A1    7/2014
EP    3227699 A    10/2017
(Continued)

OTHER PUBLICATIONS

Homann H, Graesslin I, Eggers H, Nehrke K, Vernickel P, Katscher U, Dossel O, Bornert P. Local SAR management by RF shimming: a simulation study with multiple human body models. Magn Reson Mater Phys 2012;25:193-204.
(Continued)

*Primary Examiner* — Gregory H Curran

(57) ABSTRACT

A magnetic resonance imaging, MRI, system (2), comprises MRI electronics, including a transmitting coil (11) for transmitting radio frequency, RF, signals and a receiving coil (12) for receiving RF signals; and/or a transmitting/receiving coil (3) for transmitting and receiving RF signals; and cables (22), connecting the transmitting coil (11), receiving coil (12) and/or transmitting/receiving coil (3) to other electronic elements. The MRI system (2) further comprises an overheating detection unit to detect potential overheating of a patient's (1) tissue and/or a part of the MRI system (2) caused by at least one part of the MRI electronics; and a distance unit (16), wherein the distance unit (16) comprises a gas chamber (5), to be arranged between the at least one part of the MRI electronics and the patient (1) and/or between the at least one part of the MRI electronics and the part of the MRI system (2) and adapted to be filled with a gas such that a distance between the patient (1) and the part of the MRI electronics and/or between the part of the MRI system (2) and the part of the MRI electronics increases when the gas chamber (5) is filled with the gas, wherein the gas chamber (5) is in a deflated state when no significant overheating is detected, and an inflation unit (15) to fill the gas chamber (5) with the gas, wherein the overheating detection unit and the distance unit (16) are interconnected such that the inflation unit (15) fills the gas chamber (5) with the gas to increase the distance between the patient (1) and the part of the MRI electronics and/or between the part of the (Continued)

MRI system (2) and the part of the MRI electronics if the overheating detection unit detects significant overheating of the patients (1) tissue and/or the part of the MRI system (2).

15 Claims, 8 Drawing Sheets

(51) Int. Cl.
  *G01R 33/34* (2006.01)
  *G01R 33/36* (2006.01)

(56) References Cited

U.S. PATENT DOCUMENTS

| | | |
|---|---|---|
| 2009/0012387 A1 | 1/2009 | Hanson et al. |
| 2010/0237869 A1 | 9/2010 | Griswold et al. |
| 2014/0103930 A1 | 4/2014 | Wang et al. |
| 2015/0268321 A1 | 9/2015 | Zhai et al. |
| 2017/0269176 A1 | 9/2017 | Weiss |
| 2018/0321341 A1 | 11/2018 | Biber |
| 2019/0107589 A1 | 4/2019 | Piron et al. |
| 2020/0025845 A1 | 1/2020 | Ferguson et al. |

FOREIGN PATENT DOCUMENTS

| | | |
|---|---|---|
| EP | 3395241 A1 | 10/2018 |
| JP | 2010252866 A | 11/2010 |
| WO | 2016087376 A1 | 6/2016 |

OTHER PUBLICATIONS https://www.gehealthcare.com/products/magnetic-resonance-imaging/air-technology -downloaded Jun. 23, 2022.

Andreas Port, Loris Albisetti, Matija Varga, Josip Marjanovic, Jonas Reber, David Brunner, Klaas Pruessmann. Liquid metal in stretchable tubes: A wearable 4-channel knee array. Proceedings ISMRM 2019 #1114.

International Search Report and Written Opinion from PCT/EP2021/080860 dated Jan. 21, 2022.

* cited by examiner

MAGNETIC RESONANCE IMAGING SYSTEM WITH PROTECTION FROM OVERHEATING

CROSS REFERENCE TO RELATED APPLICATIONS

This application is a U.S. national phase application of International Application No. PCT/EP2021/080860 filed Nov. 8, 2021, which claims the benefit of EP Application Serial No. 20207417.5 filed on Nov. 13, 2020 and is incorporated herein by reference.

FIELD OF THE INVENTION

The invention relates to a magnetic resonance imaging (MRI) system and a method for operating a magnetic resonance imaging system.

BACKGROUND OF THE INVENTION

Magnetic resonance imaging (MRI) systems have been widely described in the literature. One important aspect of MRI systems is the safety of the patients. In particular, an absorption of radio frequency electromagnetic fields can lead to burns and consequently to necrotic tissues if the electromagnetic field strength, the specific absorption rate of the tissue and/or the exposure time are too large.

A magnetic resonance imaging system for acquiring magnetic resonance data from a subject within an imaging zone is described in US patent application US 2017/0269176 A1. The magnetic resonance imaging system comprises a magnetic resonance imaging antenna comprising a plurality of loop antenna elements. The magnetic resonance imaging antenna further comprises multiple infrared thermometry sensors, wherein the magnetic resonance imaging antenna is configured for being positioned adjacent to an external surface of the subject, such that at least a portion of the multiple infrared thermometry sensors becomes directed towards the external surface when the magnetic resonance imaging antenna is positioned adjacent to the external surface of the subject. The magnetic resonance imaging system further comprises a memory containing machine executable instructions and pulse sequence instructions, and a processor for controlling the magnetic resonance imaging system. The processor acquires the magnetic resonance data by controlling the magnetic resonance imaging system with the pulse sequence instructions, repeatedly measures at least one surface temperature of the subject with the multiple infrared thermometry sensors during acquisition of the magnetic resonance data and performs a predefined action if the at least one surface temperature is above a predefined temperature, for reducing the risk of the subject becoming overheated. The predefined action is described as any one of the following: halt the acquisition of the magnetic resonance data, modify the pulse sequence instructions, increase air ventilation to the subject, and pause the acquisition of the magnetic resonance data. However, the described actions that can be performed to reduce the risk of the subject becoming overheated might react too slowly to actually prevent burns, especially for high field MRI scanners. Japanese patent application JP 2010-252866 A discloses a magnetic resonance imaging apparatus that comprises a plurality of airbags arranged on the wall surface of the inner wall of the bore. Said airbags are inflated after a subject is carried into the bore to prevent the subject from touching the wall surface of the inner wall of the bore during imaging. After imaging is finished, the airbags are deflated and the subject is carried out.

SUMMARY OF THE INVENTION

It is an object of the present invention to provide a magnetic resonance imaging (MRI) system and a method for operating a magnetic resonance imaging system that feature an overheating protection with a short reaction time to protect a patient's tissue from burns. It is a further object of the present invention to provide an MRI system and a method for operating an MRI system that feature an overheating protection for parts of the MRI system.

In an aspect of the present invention, a magnetic resonance imaging (MRI) system, comprising MRI electronics, an overheating detection unit and a distance unit is provided.

The MRI electronics include, among others, a transmitting coil for transmitting radio frequency (RF) signals and a receiving coil for receiving RF signals. Alternatively or additionally, the MRI electronics includes a combined transmitting/receiving coil for transmitting and receiving RF signals. Further, the MRI electronics includes cables that connect the transmitting coil, receiving coil and/or transmitting/receiving coil to other electronic elements.

The overheating detection unit is adapted to detect a potential overheating of a patient's tissue caused by at least one part of the MRI electronics. The patient is usually a human being, but also animals may be patients. The potential overheating of the patient's tissue is preferably detected with only a very short delay. Alternatively or additionally, the overheating detection unit is adapted to detect potential overheating of a part of the MRI system caused by the at least one part of the MRI electronics. Said detection is also preferably performed with only a very short delay to keep parts, especially sensitive and/or expensive parts, of the MRI system from overheating.

There are many possible events that may result in overheating caused by the part of the MRI electronics. As an example, electronic components such as capacitors in a coil, e.g., a body coil or a local receiving coil, may become loose. This may result in detuning and/or undefined distribution of radio-frequency currents, which in turn results in high local electric fields. As another example, resonant traps and/or baluns may become detuned due to mechanical vibrations or a pull on cables. This may then result in desoldering of said resonant traps and/or baluns which in turn may lead to high electric fields that may cause overheating. As yet another example, a slight change in position of the patient may lead to local electric fields that are higher than expected and/or calculated and may therefore cause overheating.

The distance unit comprises a gas chamber and an inflation unit. The gas chamber is to be arranged between the at least one part of the MRI electronics and the patient and/or between the at least one part of the MRI electronics and the part of the MRI system. This may be achieved in several ways. For example, when flexible coils are used that are laid directly onto the patient, the gas chamber may be attached to a patient's side of the transmitting coil, the receiving coil and/or the transmitting/receiving coil. The gas chamber may also be attached to cables that connect the transmitting coil, receiving coil and/or the transmitting/receiving coil to other electronic elements. As another example, if the coils are arranged underneath the patient, i.e., underneath a patient's bed, the gas chamber may be placed between a mattress and the patient, the gas chamber may be integrated into the mattress and/or the gas chamber may be arranged in a recess of the mattress. As yet another example, the gas chamber may be attached to an inner bore wall of the MRI system, protecting both the patient from burns and the MRI system from overheating. As yet another example, the gas chamber may be like a wear to be put around the arms, legs and/or local extremities of the patient. The gas chamber is adapted to be filled with a gas such that a distance between the patient and the part of the MRI electronics and/or between the part of the MRI system and the part of the MRI electronics increases when the gas chamber is filled with the gas. When no potential overheating is detected, the gas chamber is in a deflated state. As soon as significant overheating is detected, the gas chamber gets filled with gas such that the gas chamber is in an inflated state. In other words, the gas chamber is in the deflated state during regular operation of the MRI system and only gets inflated if significant overheating is detected, i.e., in an emergency. Further, when the gas chamber gets inflated, the regular operation of the MRI system is stopped. A thickness of the gas chamber in the inflated state is greater than the thickness of the gas chamber in the deflated state and this difference in thicknesses is the distance by which the part of the MRI electronics gets moved away from the patient and/or the part of the MRI system. In many cases, a distance of 10 mm to 20 mm is sufficient to protect the patient's tissue from overheating and therefore from a burn that might lead to necrotic tissues and/or to protect the part of the MRI system from overheating and being damaged.

The inflation unit is adapted to fill the gas chamber with the gas if the overheating detection unit detects significant overheating of the patient's tissue and/or of the part of the MRI system. In this context, significant overheating is to be understood as overheating that may lead to burns of the patient or to damage to the part of the MRI system. To achieve this, the overheating detection unit and the distance unit are interconnected such that when the overheating detection unit detects significant overheating of the patient's tissue and/or of the part of the MRI system, the inflation unit is triggered to fill the gas chamber with the gas such that the distance between the patient and the part of the MRI electronics and/or between the part of the MRI system and the part of the MRI electronics is increased.

The gas chamber can be filled with gas very rapidly, such that the time between the detection of the significant overheating of the patient's tissue and/or the part of the MRI system and the distancing of the part of the MRI electronics from the patient and/or the part of the MRI system is very short and damage to the patient's tissue and/or the part of the MRI system can be avoided.

The overheating detection unit may comprise at least one temperature sensor to provide temperature signals that are analyzed to detect potential overheating and to be placed on or close to the patient's skin. Hence, the temperature sensor directly measures the temperature of the patient's skin and can detect overheating close to the patient's skin. The placement of the temperature sensors is preferably chosen such that the temperature sensors are in locations that are prone to overheating, which may be determined for example by experience or through a simulation. Alternatively or additionally, the temperature sensor may be located in the MRI system, in particular next to parts of the MRI electronics. The placement of the temperature sensors in the MRI system is again preferably chosen such that the temperature sensors are in locations that are prone to overheating, e.g., certain locations of the coils or the cables. Alternatively or additionally, the temperature sensor may be attached to or integrated in the gas chamber. Said temperature sensors may react very quickly to a change in temperature and therefore trigger the inflation of the gas chamber.

The temperature sensor may be adapted to be supplied by energy that the temperature sensor extracts from the RF signal transmitted by the transmitting coil and/or transmitting/receiving coil. Therefore, no separate energy supply for the temperature sensor is needed and the temperature sensor may operate whenever an RF signal is transmitted by the transmitting coil and/or transmitting/receiving coil.

The temperature sensor may comprise a temperature sensing element and a temperature measurement may be based on optical, chemical and/or electric characteristics of the temperature sensing element.

The temperature sensor may further comprise a wireless communication unit to transmit the temperature information. Hence, no wired connection between the temperature sensor and the remainder of the MRI system is required. Therefore, the temperature sensor can be easily placed at the optimal locations without adding wires to the MRI system. Said temperature sensor may be flat and an adhesive may be applied to one side of the temperature sensor such that the temperature sensor can be used as a sticker.

The wireless communication unit may be adapted to transmit temperature RF signals at a frequency close to or equal to the radio frequency of the MRI system. The temperature information may, for example, be encoded in a modulation of the RF signal. The temperature RF signals are picked up by the receiving coil and/or transmitting/receiving coil of the MRI system. In order to protect the electronics processing the received RF signals, it may be necessary to detune the receiving coils. The MRI system may further comprise a signal analysis unit, wherein the signal analysis unit or parts of the signal analysis unit, e.g., a preamplifier and/or an integrated circuit, are adapted to receive and process the temperature RF signals.

Alternatively, the temperature sensor may have an optical connection, in particular via glass fibers, to the remainder of the MRI system. Hence, no electrical wires that might disturbed the MRI system are added to the MRI system.

The temperature sensor may be further adapted to transmit secondary information, e.g., information about its identity and/or location. The identity of the temperature sensor may be a serial number or some other number assigned to the temperature sensor. When the temperature sensors are placed on the patient's skin or in the MRI system, location data of the temperature sensor may be assigned to the identity of the temperature sensor. That way, when temperature information from a temperature sensor is received together with the secondary information, the location of the temperature sensor can be mapped to said temperature sensor.

The overheating detection unit may comprise a computing system that is adapted to analyze temperature signals and to trigger the inflation unit if significant overheating of the patient's tissue and/or the part of the MRI system is detected. Said analysis may be based, inter alia, on the absolute temperature of the temperature sensor, the increase in temperature of the temperature sensor, the location of the temperature sensor, and/or the location of the gas chamber. The analysis may be further based on the patient's information, e.g., the age and the weight of the patient and whether the patient is anesthetized and/or handicapped. The computing system to analyze the temperature signals may be based on an algorithm, such as a decision tree or a discriminator model, and/or on artificial intelligence, which may combine the different data in complex ways. Additionally and/or alternatively, the computing system may be adapted to analyze MRI system malfunctioning signals, e.g., when a cooling fan quits working and/or a short circuit is detected, in particular in the MRI electronics, since such events may also lead to an overheating of the patient's tissue or the part of the MRI system.

The gas chamber may comprise a plurality of gas subchambers and/or gas ducts. Hence, the gas chamber features increased stability when it is in the inflated state and the distancing of the patient from the parts of the MRI electronics may be performed more reliably. At least some of the gas subchambers and/or gas ducts may be connected to one another such that the gas subchambers and/or gas ducts connected to one another may be inflated by a single inflation device of the inflation unit. The walls of the gas subchambers and/or gas ducts may be made of an elastic material such that the gas chamber is self-inflatable. The inflation unit may therefore just open a valve to allow gas, in particular air, to enter the gas chamber.

The inflation unit may comprise a gas generating unit, e.g., an explosive unit and/or a compressed gas unit. In the explosive unit, a chemical reaction produces large amounts of gas and in the compressed gas unit, a compressed gas expands to a large volume when it is released. The generation of gas by the gas generating unit occurs very fast such that the gas chamber is inflated rapidly. To monitor the correct activation of the inflation unit and the correct inflation of the gas chamber, a pressure sensor inside the gas chamber may sense the gas pressure inside the gas chamber and send the measured pressure data to the MRI system. If the measured pressured data indicates a malfunctioning of the distance unit, a warning is issued and/or other measures are taken to protect the patient's tissue from overheating. Further, the distance unit may comprise a safety valve or a special structured part to prevent an explosion of the distance unit in case of a malfunctioning of the distance unit. Said safety valve may be arranged at the inflation unit, at a connecting piece between the inflation unit and the gas chamber and/or at the gas chamber.

The distance unit may be removable from the MRI system and exchangeable. Hence, if, e.g., the gas chamber cannot be returned to its deflated state, the inflation unit cannot be recharged after the distance unit has been triggered and/or the distance unit needs to be replaced after a predetermined service interval, the distance unit may be exchanged, wherein the used distance unit is detached from the MRI system and disposed of and a new distance unit is attached to the MRI system, and the remainder of the MRI system can be re-used. Another reason for exchanging the distance unit is that the distance unit may need servicing, in which case the distance unit is exchanged, then serviced and re-attached at a later time, after the service. The attachment of the distance unit to the remainder of the MRI system may be performed, e.g., by hook-and-loop fasteners, which provides a secure and tight attachment but also enables a fast and easy removal of the distance unit. Said removable and exchangeable distance unit may further comprise the temperature sensor.

In another aspect of the present invention, a method for operating a magnetic resonance imaging (MRI) system is provided. Said MRI system may be an MRI system as described above.

During an MRI scan, a transmitting coil and/or a transmitting/receiving coil of MRI electronics of the MRI system transmits a radio frequency (RF) signal to a patient. An overheating detection unit of the MRI system checks whether a potential overheating of the patient's tissue and/or a part of the MRI system caused by at least one part of the MRI electronics occurs. Such overheating can lead to burns, necrotic tissues and/or damage to the MRI system and is therefore to be avoided.

If the overheating detection unit detects significant overheating of the patient's tissue and/or a part of the MRI system, the overheating detection unit activates an inflation unit of a distance unit of the MRI system that fills a gas chamber of the distance unit with gas. Said gas chamber is arranged between the patient and the part of the MRI electronics and/or between the part of the MRI system and the part of the MRI electronics such that the distance between the patient and/or the part of the MRI system and the part of the MRI electronics increases. Said increase in distance between the patient and/or the part of the MRI system and the part of the MRI electronics protects the patient's tissue and/or the part of the MRI system from overheating and therefore from a burn that might lead to necrotic tissue and/or from damage to sensitive and/or expensive parts of the MRI system.

The overheating detection unit may check the potential overheating of the patient's tissue and/or the part of the MRI system while the transmitting coil and/or transmitting/receiving coil transmits the RF signal. Hence, there is no extra time needed to check the potential overheating of the patient's tissue and/or the part of the MRI system and the scheduling of an MRI sequence does not have to allow for the overheating detection check.

Depending on the amount of potential overheating of the patient's tissue and/or the part of the MRI system determined by the overheating detection unit, one of several steps may be performed. If only a slight overheating of the patient's tissue and/or the part of the MRI system is detected, a specific absorption rate of an MRI sequence may be reduced, e.g. by reducing the power of the RF signal, and a current MRI scan can continue, albeit with changed parameters. If a medium overheating of the patient's tissue and/or the part of the MRI system is detected, a current MRI scan may be stopped. After eliminating the cause for the overheating of the patient's tissue and/or the part of the MRI system by MRI personnel, e.g., by re-aligning cables, the MRI scan can be continued. And if a significant overheating of the patient's tissue and/or the part of the MRI system is detected, the inflation unit is activated to inflate the gas chamber. Along with the activation of the inflation unit, the MRI scan may also be stopped. Since the activation of the inflation unit may render the distance unit unusable, the distance unit may have to be exchanged before the MRI scan can be continued.

It shall be understood that a preferred embodiment of the invention can also be any combination of the dependent claims with the respective independent claim.

These and other aspects of the invention will be apparent from and elucidated with reference to the embodiments described hereinafter.

BRIEF DESCRIPTION OF THE DRAWINGS

In the following, preferred embodiments of the invention will be described, by way of example only, and with reference to the drawings in which.

DETAILED DESCRIPTION OF EMBODIMENTS

Like numbered elements in these Figs. are either equivalent elements or perform the same function. Elements which have been discussed previously will not necessarily be discussed in later Figs. if the function is equivalent.

Figure 1A:
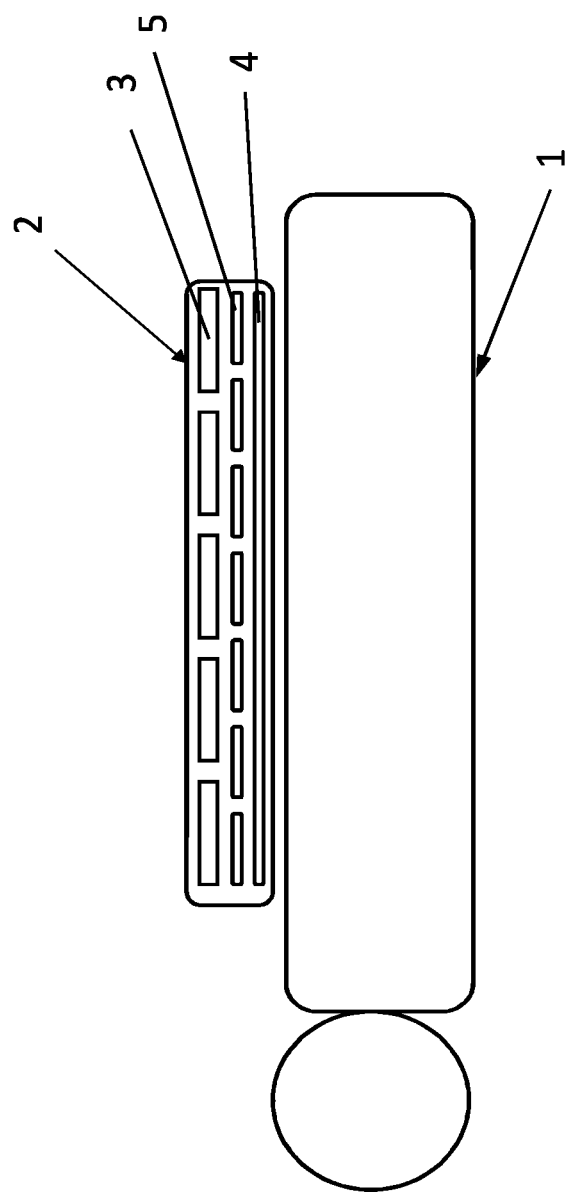
FIG. 1a shows a schematic cross-section of a patient and one embodiment of an MRI system.

FIG. 1a shows a schematic cross-section of a patient 1 and one embodiment of a magnetic resonance imaging (MRI) system 2. The MRI system 2 comprises a lightweight and flexible transmitting/receiving coil 3 that has been laid on the patient.

With higher field strengths, shorter scan times, and in particular coils 3 that are placed close to the patient 1, the risk of overheating of the patient's 1 tissue and consequently burns has increased. Also, such burns are often not noticed by the patient 1, especially if the patient 1 is anesthetized. To protect the patient 1 from possible burns, the MRI system 2 further comprises an overheating detection unit and a distance unit, wherein the overheating detection unit is realized as a temperature sensing mat 4 and only a gas chamber 5 of the distance unit is shown in FIG. 1a.

The temperature sensing mat 4 measures a temperature close to the patient's 1 skin. These temperature measurements are analyzed by a computing system that is not shown in this FIG. If it is determined by the computing system that the temperature measurements indicate significant overheating of the patient's 1 tissue, the computing system instructs the distance unit to fill the gas chamber 5 with a gas.

Figure 1B:
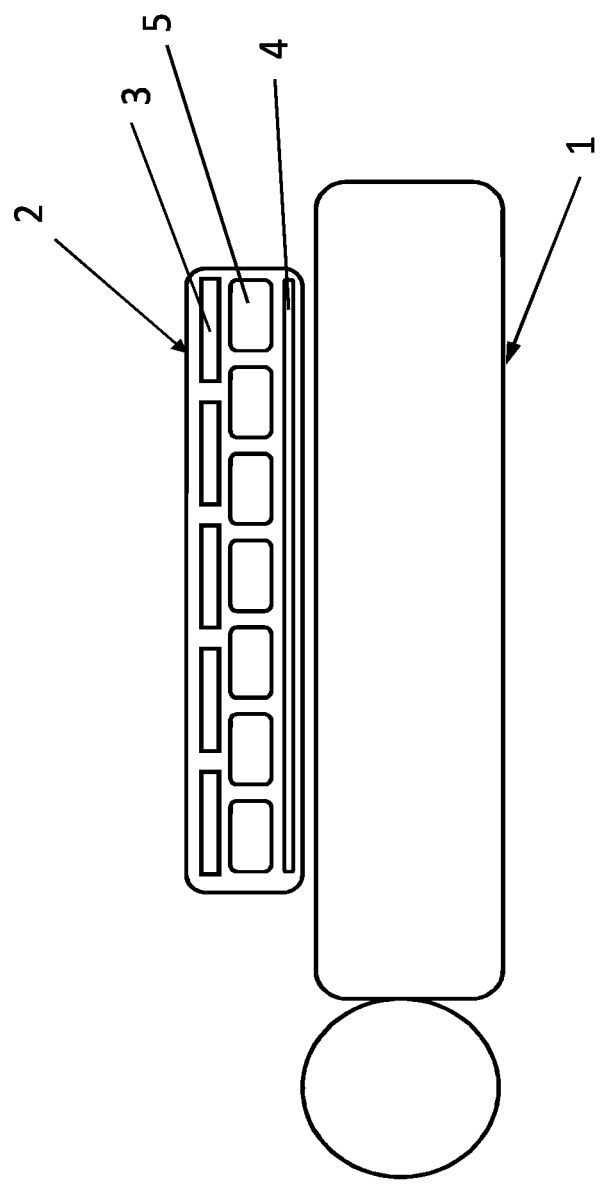
FIG. 1b shows the cross-section of FIG. 1a with a gas chamber of the MRI system filled with gas.

The MRI system 2 with the gas chamber 5 filled with a gas is shown in FIG. 1b. By filling the gas chamber 5 with a gas, a distance between the patient 1 and the transmitting/receiving coil 3 is increased and therefore the risk of overheating the patient's 1 tissue is reduced.

Figure 2:
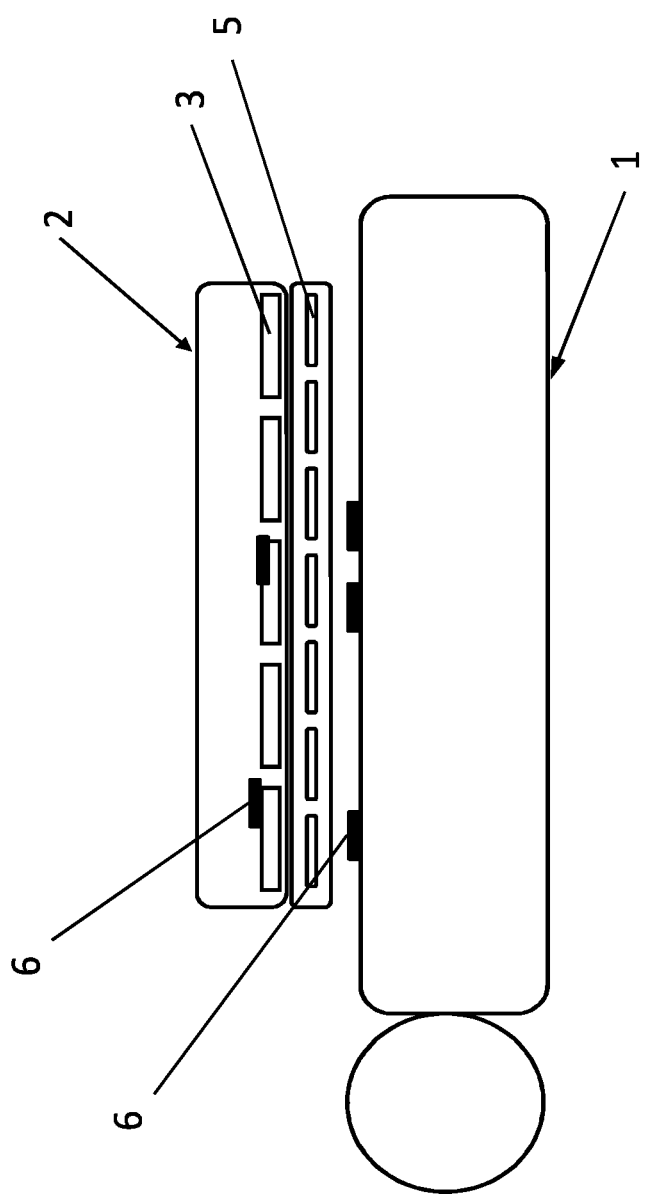
FIG. 2 shows a schematic cross-section of a patient and another embodiment of an MRI system.

FIG. 2 shows a schematic cross-section of a patient and another embodiment of an MRI system 2. In this embodiment of the MRI system 2, the overheating detection unit comprises a plurality of temperature sensors 6. Said temperature sensors 6 have one sticky side such that they may be attached to different surfaces. In the embodiment of FIG. 2, some of the temperature sensors 6 are attached to the patient's 1 skin, preferably at locations of the skin that are prone to overheating. Others of the temperature sensors 6 are attached to the transmitting/receiving coils 3, preferably at locations of the transmitting/receiving coils 3 that are prone to overheating, e.g., due to the breaking of a wire of the coils 3.

In FIG. 2, the distance unit, which contains the gas chamber 5, is a separate module that can be removed from the remainder of the MRI system, in particular from a module containing the transmitting/receiving coils 3. Hence, the distance unit may be exchanged if the distance unit has been activated and cannot be returned to its original state. The attachment of the distance unit to the remainder of the MRI system can be performed, e.g., by hook-and-loop fasteners.

Figure 3:
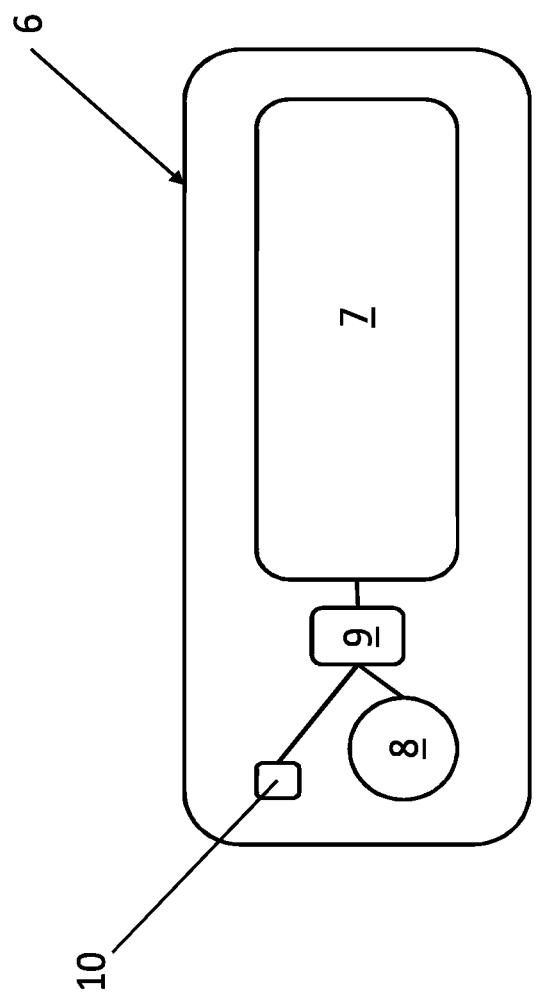
FIG. 3 shows a schematic view of one embodiment of a temperature sensor.

FIG. 3 shows a schematic view of one embodiment of a temperature sensor 6. The temperature sensor 6 comprises a radio frequency (RF) coil 7 to receive RF waves to power the temperature sensor 6 and to transmit the temperature measurements of the temperature sensor 6. The temperature sensor 6 further comprises a temperature sensing element 8, which measures the temperature based on optical, chemical and/or electric characteristics. The temperature sensor 6 further comprises sensor electronics 9 that are adapted to receive power from the RF waves, encode the temperature measurement from the temperature sensing element 8 and transmit the encoded temperature measurement via the RF coil 7. The temperature sensor 6 may also include a sensor identifier 10 that identifies the sensor by, e.g., a serial number and the sensor electronics 9 are further adapted to also transmit the sensor identification via the RF coil 7.

Figure 4:
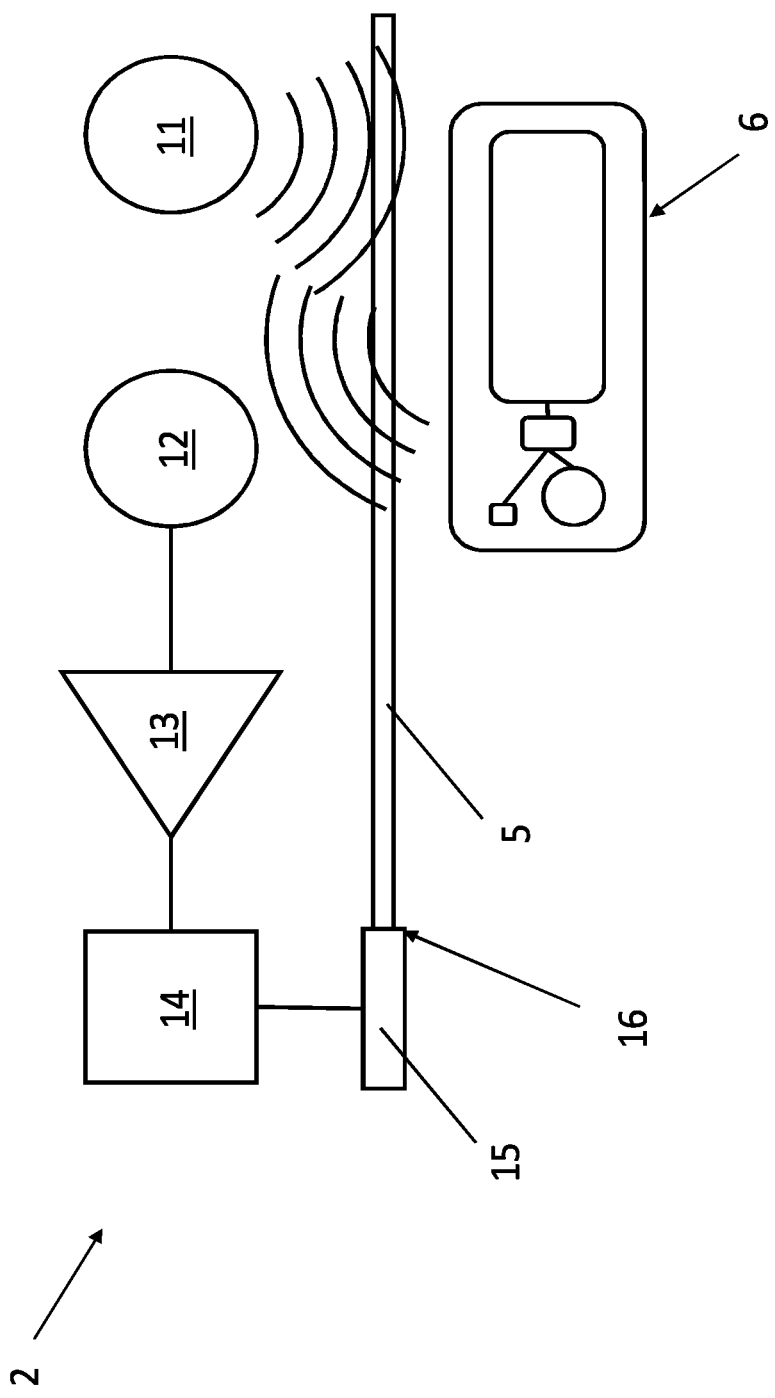
FIG. 4 shows a schematic view of another embodiment of an MRI system.

FIG. 4 shows a schematic view of another embodiment of an MRI system 2. During an MRI scan, a transmitting coil 11 of the MRI system 2 transmits RF waves. These RF waves are also used by the temperature sensor 6 to power the temperature sensor 6. The temperature sensor 6 emits RF waves that contain encoded information about the measured temperature. Said RF waves emitted by the temperature sensor 6 are received by a receiving coil 12 of the MRI system 2. A preamplifier 13 amplifies the received RF signal and extracts the temperature information from the RF waves. The temperature information is then fed to a computing system 14, which is preferably based on artificial intelligence. The computing system 14 analyses the received temperature signals and determines whether there is an imminent risk of overheating of the patient's tissue. If significant overheating is determined by the computing system 14, the computing system 14 instructs an inflation unit 15 of the distance unit 16 to fill the gas chamber 5 with gas such that the distance between the patient and the transmitting coils 11 and receiving coils 12 is increased and the risk of overheating of the patient's 1 tissue is reduced.

Figure 5:
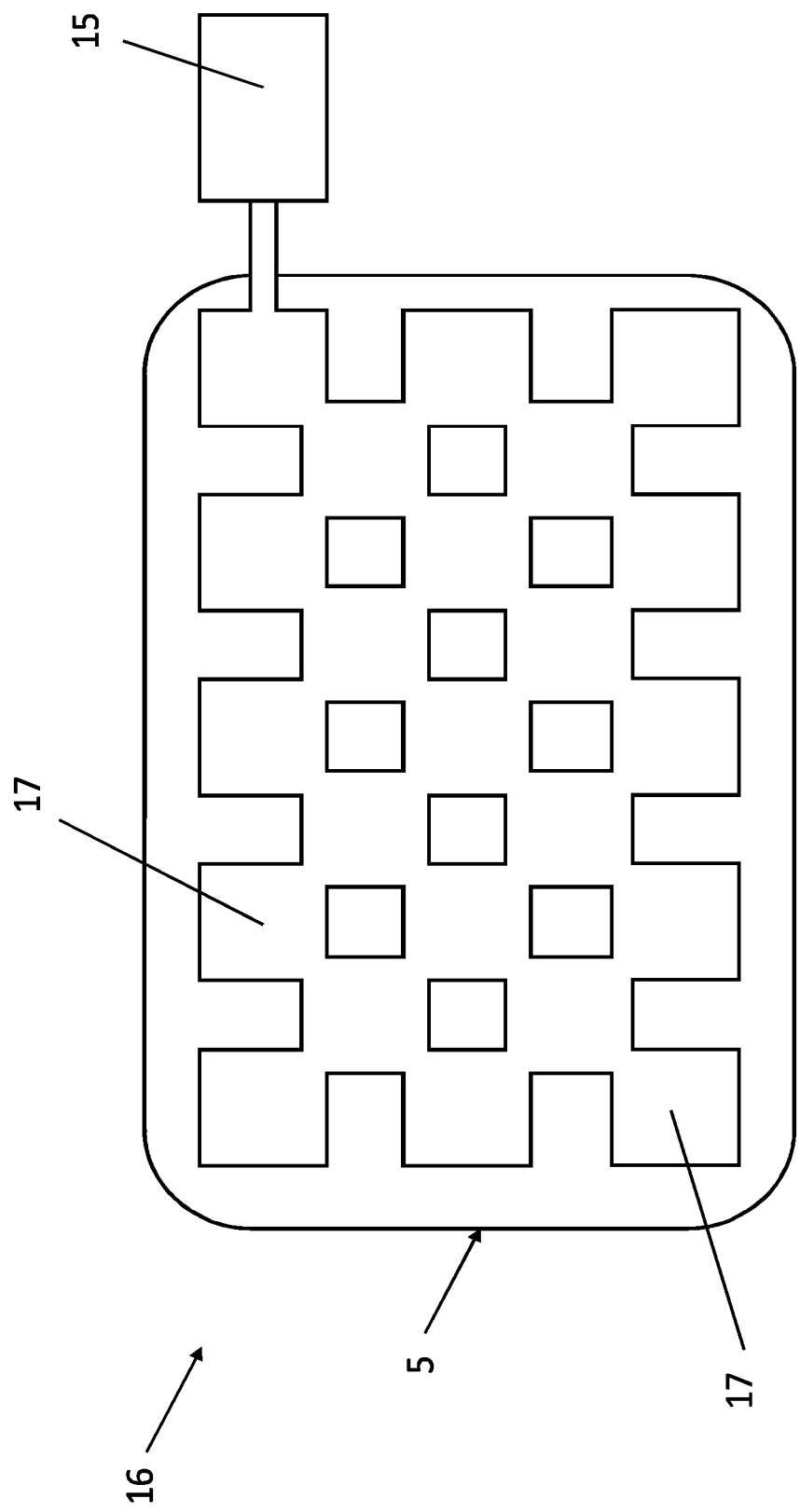
FIG. 5 shows a horizontal cross-section of one embodiment of a gas chamber.

FIG. 5 shows a horizontal cross-section of one embodiment of a gas chamber 5, comprising a plurality of gas subchambers 17. Said gas subchambers 17 are connected to one another and are connected to the inflation unit 15. When the inflation unit 15 is activated, it fills the gas subchambers 17 with a gas. The structure provided by the gas subchambers 17 provides extra stability to the gas chamber 5.

Figure 6:
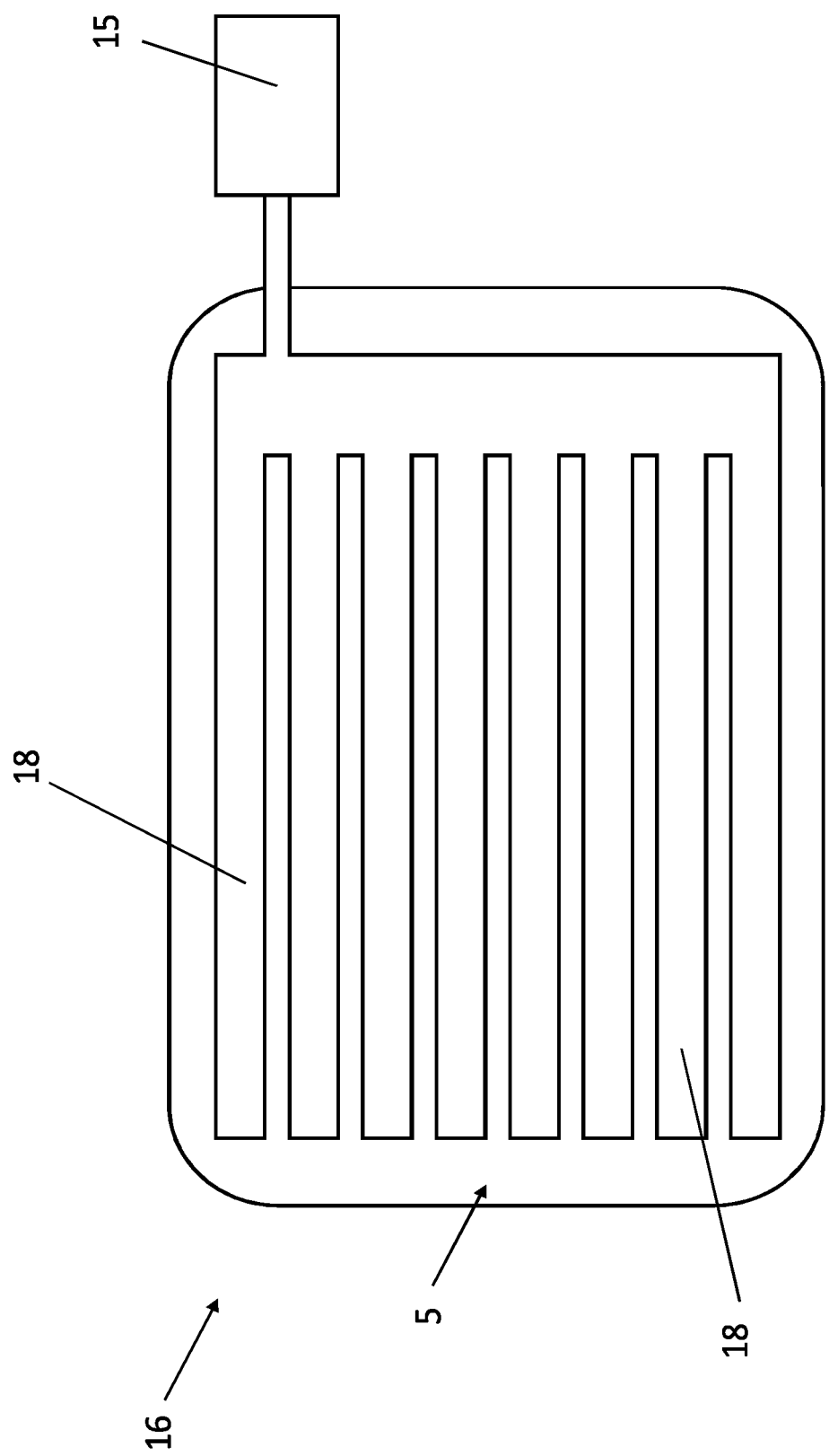
FIG. 6 shows a horizontal cross-section of another embodiment of a gas chamber.

FIG. 6 shows a horizontal cross-section of another embodiment of a gas chamber 5, comprising a plurality of gas ducts 18. Said gas ducts 18 are connected to one another and are connected to the inflation unit 15 such that an activation of the inflation unit 15 causes the gas ducts 18 to be filled with a gas. The structure provided by the gas ducts 18 provides extra stability in the longitudinal direction of the gas chamber 5.

Figure 7:
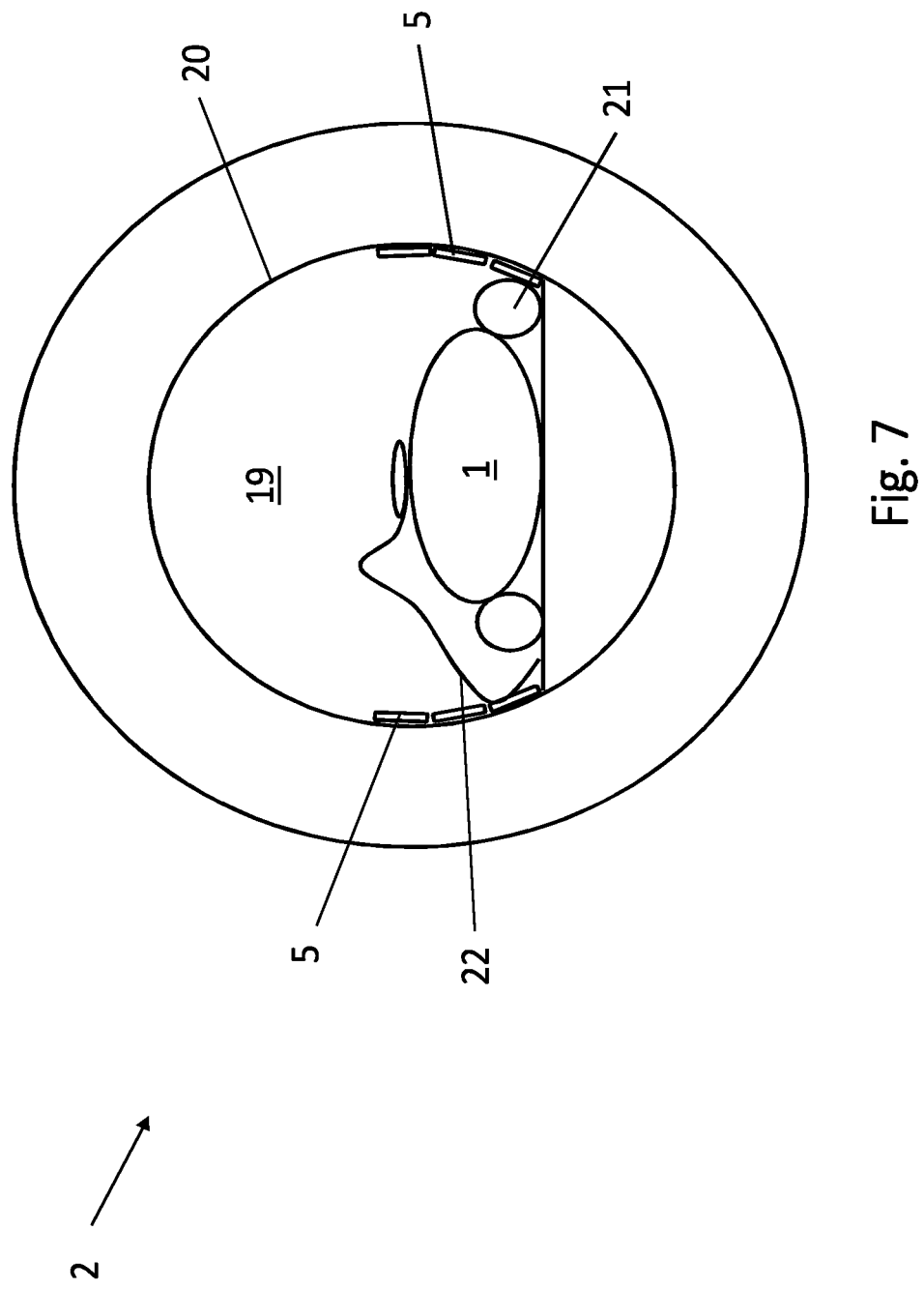
FIG. 7 shows a schematic cross-section of a patient and yet another embodiment of an MRI system.

FIG. 7 shows a schematic cross-section of a patient 1 inside an inner bore 19 of yet another embodiment of an MRI system 2. The gas chambers 5 of the distance unit are square pads that are attached to a wall 20 of the inner bore 19. A typical side length of the square pads is between 10 cm and 30 cm, preferably around 20 cm.

In the embodiment of FIG. 7, an arm 21 of the patient 1 is located close to the wall 20 of the inner bore 19. If significant overheating of the patient's 1 arm 21 is detected, the gas chambers 5 of the distance unit 16 that are located closest to the region of the patient's 1 arm 21 that may be overheated are activated to increase the distance between the patient's 1 arm 21 and the wall 20 of the inner bore 19 and hence protect the patient's 1 arm 21 from overheating.

Further, a cable 22 of the MRI system 2 is located close to the wall 20 of the inner bore 19. If significant overheating of the MRI system 2, e.g., due to a breaking of the cable 22, is detected, the gas chambers 5 of the distance unit 16 that are located closest to the region of the MRI system 2 where the cable 22 is close to the wall 20 of the inner bore 19 are activated to increase the distance between the cable 22 and the wall 20 of the inner bore 19 and hence protect the MRI system 2 from overheating.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SIGNS 1 patient
2 magnetic resonance imaging system
3 transmitting/receiving coil
4 temperature sensing mat
5 gas chamber
6 temperature sensor
7 radio frequency coil
8 temperature sensing element
9 sensor electronics
10 sensor identifier
11 transmitting coil
12 receiving coil
13 preamplifier
14 computing system
15 inflation unit
16 distance unit
17 gas subchamber
18 gas duct
19 inner bore
20 wall
21 arm
22 cable

The invention claimed is:

1. A magnetic resonance imaging (MRI) system, comprising:
MRI electronics, including
at least one of a transmitting coil for transmitting radio frequency (RF) signals and a receiving coil for receiving RF signals or
a transmitting/receiving coil configured to transmit and receive RF signals; and
cables, connecting the at least one of the transmitting coil, receiving coil or the transmitting/receiving coil to other electronic elements;
an overheating detection unit to detect potential overheating of a patient's tissue and/or a part of the MRI system caused by at least one part of the MRI electronics; and
a distance unit,
wherein the distance unit comprises
a gas chamber, to be arranged between the at least one part of the MRI electronics and the patient and/or between the at least one part of the MRI electronics and the part of the MRI system and adapted to be filled with a gas such that a distance between the patient and the part of the MRI electronics and/or between the part of the MRI system and the part of the MRI electronics increases when the gas chamber is filled with the gas, wherein the gas chamber is in a deflated state when no significant overheating is detected, and
an inflation unit to fill the gas chamber with the gas, wherein the overheating detection unit and the distance unit are interconnected such that the inflation unit fills the gas chamber with the gas to increase the distance between the patient and the part of the MRI electronics and/or between the part of the MRI system and the part of the MRI electronics if the overheating detection unit detects significant overheating of the patient's tissue and/or the part of the MRI system.

2. The magnetic resonance imaging system according to claim 1, wherein the overheating detection unit comprises at least one temperature sensor to provide temperature signals that are analyzed to detect potential overheating and to be placed on or close to the patient's skin and/or located in the MRI system, in particular next to parts of the MRI electronics.

3. The magnetic resonance imaging system according to claim 2, wherein the temperature sensor is adapted to be supplied by energy that the temperature sensor extracts from the at least one of the RF signal transmitted by the transmitting coil and/or transmitting/receiving coil.

4. The magnetic resonance imaging system according to claim 2, wherein the temperature sensor comprises a temperature sensing element and a temperature measurement is based on optical, chemical and/or electric characteristics of the temperature sensing element.

5. The magnetic resonance imaging system according to claim 2, wherein the temperature sensor further comprises a wireless communication unit to transmit the temperature information.

6. The magnetic resonance imaging system according to claim 5, wherein the wireless communication unit is adapted to transmit temperature RF signals at a frequency close to or equal to the radio frequency of the MRI system and the MRI system comprises a signal analysis unit, wherein the signal analysis unit or parts of the signal analysis unit are configured to receive and process the temperature RF signals.

7. The magnetic resonance imaging system according to claim 2, wherein the temperature sensor is further adapted to transmit secondary information.

8. The magnetic resonance imaging system according to claim 2, wherein the overheating detection unit comprises a computing system including artificial intelligence that is adapted to analyze at least one of temperature signals or MRI system malfunctioning signals, wherein the artificial intelligence is dependent on the patient's information, and to trigger the inflation unit if significant overheating of the patient's tissue and/or the part of the MRI system is detected.

9. The magnetic resonance imaging system according to claim 1, wherein the gas chamber comprises at least one of a plurality of gas subchambers or gas ducts, wherein at least some of the gas subchambers and gas ducts are connected to one another.

10. The magnetic resonance imaging system according to claim 9, wherein walls of at least one of the gas subchambers or the gas ducts are made of an elastic material such that the gas chamber is self-inflatable.

11. The magnetic resonance imaging system according to claim 1, wherein the inflation unit comprises a gas generating unit.

12. The magnetic resonance imaging system according to claim 1, wherein the distance unit is removable from the MRI system and exchangeable.

13. A method for operating the magnetic resonance imaging (MRI) system of claim 1, wherein,
  at least one of the transmitting coil or transmitting/receiving coil of MRI electronics of the MRI system transmits a radio frequency, RF, signal to a patient;
  an overheating detection unit of the MRI system checks at least one of potential overheating of the patient's tissue or a part of the MRI system caused by at least one part of the MRI electronics occurs; and
  if the overheating detection unit detects significant overheating of the at least one of the patient's tissue and/or the part of the MRI system, the overheating detection unit activates an inflation unit of a distance unit of the MRI system that fills a gas chamber of the distance unit that is arranged between the patient and the part of the MRI electronics and/or between the part of the MRI system and the part of the MRI electronics with gas such that the distance between the patient and the part of the MRI electronics and/or between the part of the MRI system and the part of the MRI electronics increases.

14. The method according to claim 13, wherein the overheating detection unit checks the potential overheating of the patient's tissue and/or the part of the MRI system while the at least one of the transmitting coil or transmitting/receiving coil transmits the RF signal.

15. The method according to claim 13, wherein, depending on the amount of potential overheating of at least one of the patient's tissue or the part of the MRI system determined by the overheating detection unit, a specific absorption rate of an MRI sequence is reduced, a current MRI scan is stopped and/or the inflation unit is activated.

* * * * *